US006407258B1

(12) United States Patent
Napierski et al.

(10) Patent No.: US 6,407,258 B1
(45) Date of Patent: Jun. 18, 2002

(54) METHOD FOR PRODUCING S-ALKYL (ARYL)-SUBSTITUTED IMIDAZOL DERIVATIVES

(75) Inventors: Bernd Napierski, Hattersheim; Heinz-Peter Rebenstock, Flörsheim; Wolfgang Holla, Kelkheim, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/601,032

(22) PCT Filed: Jan. 19, 1999

(86) PCT No.: PCT/EP99/00289

§ 371 (c)(1), (2), (4) Date: Jul. 26, 2000

(87) PCT Pub. No.: WO99/37620

PCT Pub. Date: Jul. 29, 1999

(30) Foreign Application Priority Data

Jan. 27, 1998 (DE) ........................................ 198 02 969

(51) Int. Cl.[7] ............................................ C07D 233/90

(52) U.S. Cl. ............................... 548/335.5; 548/341.5; 548/342.5

(58) Field of Search .......................... 548/335.5, 341.5, 548/342.5

(56) References Cited

U.S. PATENT DOCUMENTS

| | | | | |
|---|---|---|---|---|
| 5,350,751 A | | 9/1994 | Wagner et al. | |
| 5,482,957 A | * | 1/1996 | Wagner et al. | 514/398 |
| 5,604,251 A | | 2/1997 | Heitsch et al. | |

FOREIGN PATENT DOCUMENTS

| | | |
|---|---|---|
| EP | 0 855 392 | 7/1998 |

OTHER PUBLICATIONS

*References mailed with prior offiec action mailed on Sep. 25, 2001.*

Caille et al., "An Expedient Synthesis of Ethyl 4(5)–Alkyl(aryl)thioimidazole–5(4)–carboxylate," Jun. 1995, Synthesis, pp. 635–637.

Deprez et al., "Sulfonylureas and Sulfonylcarbamates as New Non–Tetrazole Angiotensin II Receptor Antagonists. Discovery of a Highly Potent Orally Active (Imidazolylbiphenylyl) Sulfonylurea (HR720)", 1995, J. Med. Chem., pp. 2357–2377.

Derwent Abstract of EP 0 855 392.

Wissmann et al., Angew. Chem. 92, No. 2, pp. 129–130 (1980).

* cited by examiner

*Primary Examiner*—Floyd D. Higel
*Assistant Examiner*—Kamal Saeed
(74) *Attorney, Agent, or Firm*—Finnegan, Henderson, Farabow, Garrett & Dunner, LLP

(57) ABSTRACT

The invention relates to a process for the preparation of compounds of the formula (I)

(I)

R1, N, HN, R2, R3 in which R(2) and R(3) independently of one another are —SR(4) or —COOR(5) and R(1), R(4) and R(5) have the meaning indicated in the description, which comprises cyclizing compounds of the formula II (II)

$H_2N$, R2, O, R1, N, H, R3 in which R(1), R(2) and R(3) have the meaning defined above, in the presence of alkylphosphonic anhydrides to give compounds of the formula (I), then purifying these in as is known per se by salt formation and, if appropriate, subsequent recrystallization and optionally removing radicals introduced for the protection of other functional groups in a manner known per se;

and their use as intermediate for the synthesis of active compounds.

20 Claims, No Drawings

METHOD FOR PRODUCING S-ALKYL (ARYL)-SUBSTITUTED IMIDAZOL DERIVATIVES

This application is a national stage filing under 35 U.S.C. § 371 of international application no. PCT/EP99/00289, filed on Jan. 19, 1999.

DESCRIPTION

Process for the preparation of S-alkyl(aryl)-substituted imidazole derivatives

The invention relates to a process for the preparation of S-alkyl(aryl)-substituted imidazole derivatives, and their use as an intermediate for the synthesis of active compounds.

In the preparation of active compounds such as, for example, pharmaceuticals for ,cardiac and circulatory disorders, S-alkyl(aryl)-substituted imidazole derivatives have proven themselves to be important intermediates in the preparation process. For example, U.S. Pat. No. 5,350,751, U.S. Pat. No. 5,482,957 or U.S. Pat. No. 5,604,251 describes the preparation of hypotensive preparations which, as active compound, contain compounds of the angiotensin II receptor antagonist type, which have an S-alkyl(aryl)-substituted imidazole radical.

European patent application application number 98100595.2 discloses S-alkyl(aryl)-substituted imidazole derivatives having a biphenylsulfonylcyanamide side chain as sodium-dependent chloride/bicarbonate exchangers, which as a result of their pharmacological properties are outstandingly suitable as antiarrhythmic pharmaceuticals having a cardioprotective component, inter alia for infarct prophylaxis, for infarct treatment and for the treatment of angina pectoris.

A process for the preparation of S-alkyl(aryl)-substituted imidazole derivatives by reaction of the acyclic aminoacrylic acid ester precursor with 4-dimethylaminopyridine (DMAP) and $PCl_5$ to give the corresponding imidazole compound is disclosed in U.S. Pat. No. 5,350,751, U.S. Pat. No. 5,482,957, U.S. Pat. No. 5,604,251 or J. C. Caille et al., Synthesis 1995, 635–637, P. Deprez et al., J. Med. Chem. 1995, 38, 2357–2377. The S-alkyl(aryl)imidazole derivatives obtained are then purified by chromatography on silica gel, the described yields being 43–84% (J. C. Caille et al. supra).

The known process for the cyclization and purification of the S-alkyl(aryl)imidazole derivatives has a number of disadvantages.

Thus the yields obtained are very low in many cases. Furthermore, the very expensive reagent DMAP used for the cyclization must be employed in a large excess (about 2 equivalents). The S-alkyl(aryl)imidazole derivatives also cannot be obtained in a chemical purity of >99% without laborious chromatography on silica gel, and crystallization or recrystallization in the majority of cases does not lead to the desired chemical purity; moreover, large amounts of solvents are necessary for this. The process is therefore not very suitable for the production of active compound on the industrial scale (preparation of kilo to ton amounts).

The object of the present invention was the development of a simple and economical method for the cyclization of the readily accessible aminoacrylic acid esters (J. C. Caille et al., supra) to give the desired S-alkyl(aryl)imidazole derivatives, and a practicable method for the purification of these compounds.

Surprisingly, it has been found that S-alkyl(aryl)imidazole derivatives can be prepared in high yields and very high purities by cyclization of the corresponding aminoacrylic acid esters in the presence of alkylphosphonic anhydrides which are inexpensive and readily available in industrial amounts, in particular of n-propylphosphonic anhydride (PPA), and subsequent purification by means of a suitable salt.

The invention therefore relates to a process for the preparation of compounds of the formula I, (I)

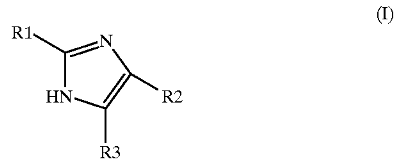

in which

R(1) is hydrogen;
- alkyl having 1, 2, 3, 4, 5, 6, 7 or 8 carbon atoms, which 4s unsubstituted or is substituted by 1, 2 or 3 identical or different radicals from the group consisting of F, Cl, Br, $CF_3$, methyl, methoxy, $NO_2$ or NR(6)R(7);
- —$C_nH_{2n}$-cycloalkyl having 1, 2, 3, 4, 5, 6 or 7 carbon atoms;
- where n is equal to 0, 1, 2 or 3;
- —$C_nH_{2n}$-phenyl, which is unsubstituted or is substituted by 1, 2 or 3 identical or different radicals from the group consisting of F, Cl, Br, $CF_3$, $NO_2$, methyl, methoxy, hydroxyl or NR(6)R(7);
- where n is equal to 0, 1, 2 or 3;
- —$C_nH_{2n}$-heteroaryl having 1, 2, 3, 4, 5, 6, 7, 8 or 9 carbon atoms, which is unsubstituted or is substituted by 1, 2 or 3 identical or different radicals from the group consisting of F, Cl, Br, $CF_3$, $NO_2$, methyl, methoxy, hydroxyl or NR(6)R(7);
- where n is equal to 0, 1, 2 or 3;

R(2) and R(3) independently of one another are —SR(4) or —COOR(5);

R(4) and R(5) independently of one another are alkyl having 1, 2, 3, 4, 5, 6, 7 or 8 carbon atoms, which is unsubstituted or is substituted by 1, 2 or 3 identical or different radicals from the group consisting of F, Cl, Br, $CF_3$, methyl, $NO_2$, methoxy or NR(6)R(7);
- —$C_nH_{2n}$-cycloalkyl having 3, 4, 5, 6 or 7 carbon atoms;
- where n is equal to 0, 1, 2 or 3;
- —$C_nH_{2n}$-phenyl, which is unsubstituted or is substituted by 1, 2 or 3 identical or different radicals from the group consisting of F, Cl, Br, $CF_3$, CN, $NO_2$, methyl, methoxy, hydroxyl or NR(6)R(7);
- where n is equal to 0, 1, 2 or 3;
- —$C_nH_{2n}$-heteroaryl having 1, 2, 3, 4, 5, 6, 7, 8 or 9 carbon atoms, which is unsubstituted or is substituted by 1, 2 or 3 identical or different radicals from the group consisting of F, Cl, Br, $CF_3$, $NO_2$, methyl, methoxy, hydroxyl or NR(6)R(7);
- where n is equal to 0, 1, 2 or 3;

R(6) and R(7) independently of one another are alkyl having 1, 2, 3 or 4 carbon atoms;

or a salt thereof, which comprises cyclizing compounds of the formula II

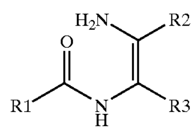

in which R(1), R(2) and R(3) have the meaning defined above, in the presence of alkylphosphonic anhydrides to give compounds of the formula (I), then purifying these in as is known per se by salt formation and, if appropriate, subsequent recrystallization and optionally removing radicals introduced for the protection of other functional groups in a manner known per se.

Suitable anhydrides according to the novel process are those of the straight- or branched-chain, optionally cyclic alkylphosphonic acids having chain lengths of 1–8 carbon atoms, preferably up to 4 carbon atoms.

The alkylphosphonic anhydrides used according to the invention are stable at room temperature. They are readily soluble in most nonaqueous solvents, in particular in lipid solvents such as chloroform or methylene chloride, but also in polar solvents such as DMF and DMA.

Particularly suitable anhydrides of the alkylphosphonic acids within the meaning of the invention are methylphosphonic anhydride, ethylphosphonic anhydride, n-propylphosphonic anhydride, n-butylphosphonic anhydride, in particular n-propylphosphonic anhydride.

The alkylphosphonic anhydrides can be prepared in a manner known per se, as formulated, for example, in Houben-Weyl, Methoden der Organischen Chemie [Methods of Organic Chemistry], G. Thieme Verl., Stuttgart 1963, Vol. XII, p. 612. The preparation of n-propylphosphanic anhydride (PPA) is possible, for example, by the process described by Wissmann and Kleiner (Angew. Chem. 92 (1980) No. 2, pp. 129–130).

The acyclic precursors (II) necessary for the preparation of the compounds of the formula (I) can easily be prepared by methods known from the literature (J. C. Caille et al., Synthesis 1995, 635; P. Deprez et al., J. Med. Chem. 1995, 38, 2357).

A preferred embodiment is one wherein compounds of the formula I are prepared in which R(1) is hydrogen;
- alkyl having 1, 2, 3, 4, 5, 6, 7 or 8 carbon atoms, which is unsubstituted or is substituted by 1 or 2 identical or different radicals from the group consisting of F, Cl, $CF_3$, methyl, methoxy, $NO_2$ or NR(6)R(7);
- —$C_nH_{2n}$-cycloalkyl having 1, 2, 3, 4, 5, 6 or 7 carbon atoms;
  where n is equal to 0, 1 or 2;
- —$C_nH_{2n}$-phenyl, which is unsubstituted or is substituted by 1 or 2 identical or different radicals from the group consisting of F, Cl, $CF_3$, $NO_2$, methyl, methoxy, hydroxyl or NR(6)R(7);
  where n is equal to 0, 1 or 2;
- —$C_nH_{2n}$-heteroaryl having 1, 2, 3, 4, 5, 6, 7, 8 or 9 carbon atoms, which is unsubstituted or is substituted by a radical from the group consisting of F, Cl, $CF_3$, $NO_2$, methyl, methoxy, hydroxyl or NR(6)R(7);
  where n is equal to 0, 1 or 2;

R(2) and R(3) independently of one another are —SR(4) or —COOR(5);

R(4) and R(5) independently of one another are alkyl having 1, 2, 3, 4, 5, 6, 7 or 8 carbon atoms, which is unsubstituted or is substituted by 1 or 2 identical or different radicals from the group consisting of F, Cl, $CF_3$, methyl, $NO_2$, methoxy or NR(6)R(7);
- —$C_nH_{2n}$-cycloalkyl having 3, 4, 5, 6 or 7 carbon atoms;
  where n is equal to 0, 1 or 2;
- —$C_nH_{2n}$-phenyl, which is unsubstituted or is substituted by 1 or 2 identical or different radicals from the group consisting of F, Cl, $CF_3$, CN, $NO_2$, methyl, methoxy, hydroxyl or NR(6)R(7);
  where n is equal to 0, 1 or 2;
- —$C_nH_{2n}$-heteroaryl having 1, 2, 3, 4, 5, 6, 7, 8 or 9 carbon atoms, which is unsubstituted or is substituted by a radical from the group consisting of F, Cl, $CF_3$, $NO_2$, methyl, methoxy, hydroxyl or NR(6)R(7);
  where n is equal to 0, 1 or 2;

R(6) and R(7) are methyl;

or a salt thereof.

A particularly preferred embodiment is one wherein compounds of the formula I are prepared in which R(1) is hydrogen;
- alkyl having 1, 2, 3, 4, 5, 6, 7 or 8 carbon atoms, which is unsubstituted or is substituted by 1 a radical from the group consisting of F, Cl, $CF_3$, methyl, methoxy, $NO_2$ or NR(6)R(7);
- cycloalkyl having 1, 2, 3, 4, 5, 6 or 7 carbon atoms;
- phenyl, which is unsubstituted or is substituted by a radical from the group consisting of F, Cl, $CF_3$, $NO_2$, methyl, methoxy, hydroxyl or NR(6)R(7);
- heteroaryl having 1, 2, 3, 4, 5, 6, 7, 8 or 9 carbon atoms, which is unsubstituted or is substituted by a radical from the group consisting of F, Cl, $CF_3$, $NO_2$, methyl, methoxy, hydroxyl or NR(6)R(7);

R(2) and R(3) independently of one another are —SR (4) or —COOR(5);

R(4) and R(5) independently of one another are
- alkyl having 1, 2, 3, 4, 5, 6, 7 or 8 carbon atoms, which is unsubstituted or is substituted by a radical from the group consisting of F, Cl, $CF_3$, methyl, $NO_2$, methoxy or NR(6)R(7);
- cycloalkyl having 3, 4, 5, 6 or 7 carbon atoms;
- phenyl, which is unsubstituted or is substituted by a radical from the group consisting of F, Cl, $CF_3$, CN, $NO_2$, methyl, methoxy, hydroxyl or NR(6)R(7);
- heteroaryl having 1, 2, 3, 4, 5, 6, 7, 8 or 9 carbon atoms, which is unsubstituted or is substituted by a radical from the group consisting of F, Cl, $CF_3$, $NO_2$, methyl, methoxy, hydroxyl or NR(6)R(7);

R(6) and R(7) are methyl;

or a salt thereof.

A very particularly preferred embodiment is one wherein compounds of the formula I are prepared in which R(1) is hydrogen;
- alkyl having 1, 2, 3, 4, 5 or 6 carbon atoms, which is unsubstituted or is substituted by 1 a radical from the group consisting of F, Cl, $CF_3$, methyl or methoxy;
- cycloalkyl having 1, 2, 3, 4, 5, 6 or 7 carbon atoms;
- phenyl, which is unsubstituted or is substituted by a radical from the group consisting of F, Cl, $CF_3$, $NO_2$, methyl or methoxy;
- heteroaryl having 1, 2, 3, 4, 5, 6, 7, 8 or 9 carbon atoms, which is unsubstituted or is substituted by a radical from the group consisting of F, Cl, $CF_3$, methyl or methoxy;

R(2) and R(3) independently of one another are —SR(4) or —COOR(5);

R(4) and R(5) independently of one another are alkyl having 1, 2, 3, 4, 5 or 6 carbon atoms, which is unsubstituted or is substituted by a radical from the group consisting of F, Cl, $CF_3$, methyl or methoxy; cycloalkyl having 3, 4, 5, 6 or 7 carbon atoms;

phenyl, which is unsubstituted or is substituted by a radical from the group consisting of F, Cl, $CF_3$, CN, methyl or methoxy;

heteroaryl having 1, 2, 3, 4, 5, 6, 7, 8 or 9 carbon atoms, which is unsubstituted or is substituted by a radical from the group consisting of F, Cl, $CF_3$, methyl or methoxy;

or a salt thereof.

Also preferred is the preparation of compounds of the formula I in which R(1) is alkyl having 1, 2, 3, 4, 5 or 6 carbon atoms and the other radicals and variables are as defined above, and their salts.

Additionally also preferred is the preparation of compounds of the formula I in which R(1) is alkyl having 1, 2, 3, 4, 5 or 6 carbon atoms;

R(2) and R(3) independently of one another are —SR(4) or —COOR(5);

R(4) is alkyl having 1, 2, 3, 4, 5 or 6 carbon atoms or —$C_nH_{2n}$-phenyl where n is equal to 0, 1 or 2 and R(5) is alkyl having 1, 2, 3, 4, 5 or 6 carbon atoms or a salt thereof.

Additionally preferred is the preparation of compounds of the formula I or a salt thereof, in which R(2) is —S(R4) and R(3) is —COOR(5), the other radicals and variables being as defined above.

Alkyl can be straight-chain or branched. Examples of alkyl radicals having 1, 2, 3, 4, 5, 6, 7 or 8 carbon atoms are: methyl, ethyl, propyl, butyl, pentyl, hexyl, heptyl, octyl, isopropyl, isobutyl, isopentyl, neopentyl, isohexyl, 3-methylpentyl, sec-butyl, tert-butyl, tert-pentyl.

Cycloalkyl radicals are in particular cyclopropyl, cyclobutyl, cyclopentyl, cyclohexyl, cycloheptyl which, however, can also be substituted, for example, by alkyl having 1, 2, 3 or 4 carbon atoms. Examples of substituted cycloalkyl radicals which may be mentioned are 4-methylcyclohexyl and 2,3-dimethylcyclopentyl.

Heteroaryl is in particular understood as meaning radicals which are derived from phenyl or naphthyl, in which one or more CH groups are replaced by N and/or in which at least two adjacent CH groups are replaced by S, NH or O (with formation of a five-membered aromatic ring). In addition, one or both atoms of the condensation site of bicyclic radicals (such as in indolizinyl) can also be nitrogen atoms.

Heteroaryl is considered in particular as furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl. Optionally occurring stereocenters can be of the (R) or (S) configuration.

The compounds of the formula II can be employed as E/Z isomer mixtures or as pure E or Z isomers. E/Z isomers can be separated into the individual isomers by chromatography.

The cyclization of the compounds of the formula (II) to compounds of the formula (I) is preferably carried out by reaction of the acyclic compounds with the inexpensive and commercially obtainable n-propylphosphonic anhydride (PPA, H. Wissmann and H.-J. Kleiner, Angew. Chem. 1980, 92, 129) in a suitable solvent. The desired compounds of the formula (I) are obtained as crude products by neutralization of the reaction mixture. For the isolation of the pure compounds of the formula (I), the crude product is treated with a suitable acid such as, for example, sulfuric acid in a suitable organic solvent with gentle cooling. The salt which precipitates is filtered off with suction and washed or recrystallized from suitable solvents. After reaction of the pure salt with base, the compounds of the formula (I) are obtained in high yield and high chemical purity.

The cyclization can be carried out in a wide variety of solvents. Suitable solvents are, for example, esters such as ethyl acetate, tert-butyl acetate, ethers such as, for example tert-butyl methyl ether, dioxane, THF, hydrocarbons and halogenated hydrocarbons such as toluene and methylene chloride. Mixtures of various solvents can also be used, such as, for example, toluene/ethyl acetate.

The sequence of addition of the reagents is unimportant. Either the acyclic compounds of the formula (II) or the alkylphosphonic anhydride, e.g. PPA, can be introduced first. It is also possible to meter both components into the reaction vessel simultaneously. Frequently, it is useful to use the commercially obtainable solutions of PPA, e.g. in ethyl acetate.

The amount of alkylphosphonic anhydride used is between 0.1–5.0 mol of alkylphosphonic anhydride per mole of compounds of the formula (II), preferably 0.2–1.0 mol of alkylphosphonic anhydride.

The cyclization is in general carried out at temperatures of 10–130° C., preferably at 20–80° C.

The reaction time is between 0.25 h and 3 days, preferably between 1 and 48 h.

For neutralization, both inorganic and organic bases are suitable, for example ammonia or amines such as, for example, triethylamine or salts such as, for example, $K_2CO_3$ or $NaHCO_3$.

The compounds of the formula I can be present as salts of sulfuric acid, e.g. as sulfates or hydrogensulfates, but also as salts of other acids which can be used for the precipitation of the imidazole compounds.

The compounds of the formula I are important intermediates for the preparation of pharmacologically active substances, such as, for example, angiotensin II receptor antagonists or sodium-dependent chloride/bicarbonate exchangers (NCBE). The conversion of the compounds of the formula I to pharmacologically active substances can in this case be carried out, for example, according to the synthesis processes described in U.S. Pat. No. 5,350,751, U.S. Pat. No. 5,482,957, U.S. Pat. No. 5,604,251, European patent application No. 98100595.2 or P. Deprez et al., J. Med. Chem. 1995, 38, 2357–2377.

EXAMPLES

Example 1

Ethyl 2-n-Butyl-4-methylthio-1H-imidazole-5-carboxylate 14 l of 50% strength PPA solution (22.9 mol) in ethyl acetate are introduced into 100 l of ethyl acetate and stirred at about 20° C. for 30 min. 10.0 kg (38.42 mol) of ethyl (E) and (Z)-3-amino-3-thiomethyl-2(n-butylcarbonyl) aminoacrylate are then introduced. The mixture is stirred at about 20° C. until everything has dissolved and heated to reflux. The reaction is complete after about 2h. The reaction mixture is cooled to 20° C., cautiously neutralized with 60 l of satd. $NaHCO_3$ soln. and the phases are separated. The organic phase is then cooled to 10° C. and treated with 2.05 l of conc. sulfuric acid. The mixture is stirred until crystallization is complete (about 20 min), then the imidazole salt is filtered off with suction and dried at 20–30° C. in vacuo; yield of imidazole salt: 11.9 kg (91%); mp 150–160° C.

For the liberation of the desired imidazole, 11.9 kg of ethyl 2-n-butyl-4-methylthio-1H-imidazole-5-carboxylate×$H_2SO_4$ are dissolved in 65 l of water, then treated with 30 l of MTB ether and then, for neutralization, with 6.2 kg of sodium hydrogencarbonate in portions. The phases are separated. The organic phase is thoroughly dried using $Na_2SO_4$. The filtrate is concentrated to dryness. The residue is treated with 50 l of petroleum ether and heated to reflux until everything has dissolved. The mixture is slowly cooled to −5 to 0° C., stirred for a further hour and the precipitated product is then filtered off. The solid obtained is washed with a little cooled petroleum ether. The product is dried in vacuo at 20–30° C. Yield: 7.85 kg (92.6%).

$C_{11}H_{18}N_2O_2S$ calc. C, 54.51 H, 7.48 N, 11.56 S 13.23; found C, 54.5 H, 7.5 N, 11.6 S 13.3; Mp: 74–76° C. 1H-NMR (200 MHz, CDCl3): δ=0.93 (t, J =7.5 Hz; 3H), 1.4 (m; 5H), 1.74 (m; 2H), 2.6 (s, 3H), 2.73 (t, J=7.5 Hz; 2H), 4.35 (q, J=7 Hz; 2H).

The compounds of Examples 2 to 5 can be prepared as follows.

Example 2

Ethyl 2-Methyl-4-ethylthio-1H-imidazole-5-carboxylate 14 ml of 50% strength PPA solution (0.023 mmol) in ethyl acetate are introduced into 100 ml of ethyl acetate and stirred at about 20° C. for 30 min. 8.83 g (0.038 mol) of ethyl (E)- and (Z)-3-amino-3-thioethyl-2(methylcarbonyl) aminoacrylate are then introduced. The mixture is stirred at about 20° C. until everything has dissolved and heated to reflux. The reaction is complete after about 2 h. The reaction mixture is cooled to 20° C., cautiously neutralized with 60 ml of satd. $NaHCO_3$ soln. and the phases are separated. The organic phase is then cooled to 10° C. and treated with about 2 ml of conc. sulfuric acid. The mixture is stirred until crystallization is complete, then the imidazole salt is filtered off with suction and dried at 20–30° C. in vacuo.

For liberation of the desired imidazole, 10.9 g (0.035 mol) of ethyl 2-methyl-4-ethylthio-1H-imidazole-5-carboxylate×$H_2SO_4$ are dissolved in about 70 ml of water, then treated with 30–40 ml of MTB ether and then, for neutralization, with about 6.2 g of sodium hydrogencarbonate in portions. The phases are separated. The organic phase is thoroughly dried using $Na_2SO_4$. The filtrate is concentrated to dryness. The residue is treated with 50–60 ml of petroleum ether and heated to reflux until everything has dissolved. The mixture is slowly cooled to −5 to 0° C., stirred for a further hour and the precipitated product is then filtered off. The solid obtained is washed with a little cooled petroleum ether. The product is dried in vacuo at 20–30° C.

Example 3

Ethyl 2-n-Propyl-4-ethylthio-1H-imidazole-5-carboxylate 14 ml of 50% strength PPA solution (0.023 mol) in ethyl acetate are introduced into 100 ml of ethyl acetate and stirred at about 20° C. for 30 min. 10 g (0.038 mol) of ethyl (E)- and (Z)-3-amino-3-thioethyl-2(n-propylcarbonyl)aminoacrylate are then introduced. The mixture is stirred at about 20° C. until everything has dissolved and heated to reflux. The reaction is complete after about 2 h. The reaction mixture is cooled to 20° C., neutralized with 60 ml of satd. $NaHCO_3$ soln. and the phases are separated. The organic phase is then cooled to 10° C. and treated with about 2 ml of conc. sulfuric acid. The mixture is stirred until crystallization is complete, then the imidazole salt is filtered off with suction and dried at 20–30° C. in vacuo.

For the liberation of the desired imidazole, 11.6 g of ethyl 2-n-propyl-4-ethylthio-1H-imidazole-5-carboxylate×$H_2SO_4$ are dissolved in about 70 ml of water, then treated with 30–40 ml of MTB ether and then, for neutralization, with about 6.2 g of sodium hydrogencarbonate in portions. The phases are separated. The organic phase is dried thoroughly using $Na_2SO_4$.The filtrate is concentrated to dryness. The residue is treated with 50–60 ml of petroleum ether and heated to reflux until everything has dissolved. The mixture is slowly cooled to −5 to 0° C., stirred for a further hour and the precipitated product is then filtered off. The solid obtained is washed with a little cooled petroleum ether. The product is dried in vacuo at 20–30° C.

Example 4

Methyl 2-n-Butyl-4-ethythio-1H-imidazole-5-carboxylate

Preparation can be carried out analogously to Example 3. Instead of ethyl (E)- and (Z)-3-amino-3-thioethyl-2(n-propylcarbonyl)aminoacrylate, 0.038 mol of methyl (E) and (Z)-3-amino-3-thioethyl-2(n-butylcarbonyl)aminoacrylate are then introduced.

Example 5

Ethyl 2-n-Butyl-4-benzylthio-1H-imidazole-5-carboxylate

Preparation can be carried out analogously to Example 3. Instead of ethyl (E)- and (Z)-3-amino-3-thioethyl-2(n-propylcarbonyl)aminoacrylate, 12.8 g (0.038 mol) of ethyl (E) and (Z)-3-amino-3-thioethyl-2(n-butylcarbonyl) aminoacrylate are then introduced.

What is claimed is:

1. A process for the preparation of a compound of the (I)

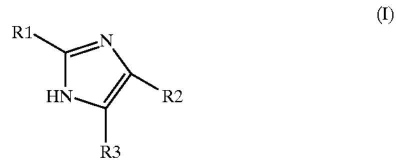

in which

R(1) is hydrogen;

alkyl having 1, 2, 3, 4, 5, 6, 7 or 8 carbon atoms, which is unsubstituted or is substituted by 1, 2 or 3 identical or different radicals from the group consisting of F, Cl, Br, $CF_3$, methyl, methoxy, $NO_2$ or NR(6)R(7);

—$C_nH_{2n}$-cycloalkyl having 1, 2, 3, 4, 5, 6 or 7 carbon atoms; where n is equal to 0, 1, 2 or 3;

—$C_nH_{2n}$-phenyl, which is unsubstituted or is substituted by 1, 2 or 3 identical or different radicals from the group consisting of F, Cl, Br, $CF_3$, $NO_2$, methyl, methoxy, hydroxyl or NR(6)R(7);

where n is equal to 0, 1, 2 or 3; or

—$C_nH_{2n}$-heteroaryl having 1, 2, 3, 4, 5, 6, 7, 8 or 9 carbon atoms, which is unsubstituted or is substituted by 1, 2 or 3 identical or different radicals from the group consisting of F, Cl, Br, $CF_3$, $NO_2$, methyl, methoxy, hydroxyl or NR(6)R(7);

where n is equal to 0, 1, 2 or 3;

R(2) and R(3) independently of one another are —SR(4) or —COOR(5);

R(4) and R(5) independently of one another are alkyl having 1, 2, 3, 4, 5, 6, 7 or 8 carbon atoms, which is unsubstituted or is substituted by 1, 2 or 3 identical or different radicals from the group consisting of F, Cl, Br, $CF_3$, methyl, $NO_2$, methoxy or NR(6)R(7);

—$C_nH_{2n}$-cycloalkyl having 3, 4, 5, 6 or 7 carbon atoms;

where n is equal to 0, 1, 2 or 3;

—$C_nH_{2n}$-phenyl, which is unsubstituted or is substituted by 1, 2 or 3 identical or different radicals from the group consisting of F, Cl, Br, $CF_3$, CN, $NO_2$, methyl, methoxy, hydroxyl or NR(6)R(7);

where n is equal to 0, 1, 2 or 3; or

—$C_nH_{2n}$-heteroaryl having 1, 2, 3, 4, 5, 6, 7, 8 or 9 carbon atoms, which is unsubstituted or is substituted by 1, 2 or 3 identical or different radicals from the group consisting of F, Cl, Br, $CF_3$, $NO_2$, methyl, methoxy, hydroxyl or NR(6)R(7);

where n is equal to 0, 1, 2 or 3; and

R(6) and R(7) independently of one another are alkyl having 1, 2, 3 or 4 carbon atoms;

or a salt thereof, which comprises cyclizing a compound of the formula II (II)

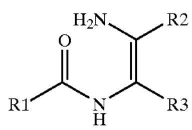

in which R(1), R(2) and R(3) have the meaning defined above, in the presence of an alkylphosphonic anhydride to give a compound of the formula (I), and, optionally, treating the compound of formula (I) with an acid to obtain a salt of the compound of formula (I).

2. The process as claimed in claim 1, wherein the compound of the formula I or salt thereof is prepared in which:

R(1) is hydrogen;

alkyl having 1, 2, 3, 4, 5, 6, 7 or 8 carbon atoms, which is unsubstituted or is substituted by 1 or 2 identical or different radicals from the group consisting of F, Cl, $CF_3$, methyl, methoxy, $NO_2$ or NR(6)R(7);

—$C_nH_{2n}$-cycloalkyl having 1, 2, 3, 4, 5, 6 or 7 carbon atoms;

where n is equal to 0, 1 or 2;

—$C_nH_{2n}$-phenyl, which is unsubstituted or is substituted by 1 or 2 identical or different radicals from the group consisting of F, Cl, $CF_3$, $NO_2$, methyl, methoxy, hydroxyl or NR(6)R(7);

where n is equal to 0, 1 or 2; or

—$C_nH_{2n}$-heteroaryl having 1, 2, 3, 4, 5, 6, 7, 8 or 9 carbon atoms, which is unsubstituted or is substituted by a radical from the group consisting of F, Cl, $CF_3$, $NO_2$, methyl, methoxy, hydroxyl or NR(6)R(7);

where n is equal to 0, 1 or 2;

R(2) and R(3) independently of one another are —SR(4) or —COOR(5);

R(4) and R(5) independently of one another are alkyl having 1, 2, 3, 4, 5, 6, 7 or 8 carbon atoms, which is unsubstituted or is substituted by 1 or 2 identical or different radicals from the group consisting of F, Cl, $CF_3$, methyl, $NO_2$, methoxy, or NR(6)R(7);

—$C_nH_{2n}$-cycloalkyl having 3, 4, 5, 6 or 7 carbon atoms; where n is equal to 0, 1 or 2;

—$C_nH_{2n}$-phenyl, which is unsubstituted or is substituted by 1 or 2 identical or different radicals from the group consisting of F, Cl, $CF_3$, CN, $NO_2$, methyl, methoxy, hydroxyl or NR(6)R(7);

where n is equal to 0, 1 or 2; or

—$C_nH_{2n}$-heteroaryl having 1, 2, 3, 4, 5, 6, 7, 8 or 9 carbon atoms, which is unsubstituted or is substituted by a radical from the group consisting of F, Cl, $CF_3$, $NO_2$, methyl, methoxy, hydroxyl or NR(6)R(7);

where n is equal to 0, 1 or 2; and

R(6) and R(7) are methyl.

3. The process as claimed in claim 1, wherein the compound of the formula I or salt thereof is prepared in which:

R(1) is hydrogen;

alkyl having 1, 2, 3, 4, 5, 6, 7 or 8 carbon atoms, which is unsubstituted or is substituted by a radical from the group consisting of F, Cl, $CF_3$, methyl, methoxy, $NO_2$ or NR(6)R(7);

cycloalkyl having 1, 2, 3, 4, 5, 6 or 7 carbon atoms;

phenyl, which is unsubstituted or is substituted by a radical from the group consisting of F, Cl, $CF_3$, $NO_2$, methyl, methoxy, hydroxyl or NR(6)R(7); or heteroaryl having 1, 2, 3, 4, 5, 6, 7, 8 or 9 carbon atoms, which is unsubstituted or is substituted by a radical from the group consisting of F, Cl, $CF_3$, $NO_2$, methyl, methoxy, hydroxyl or NR(6)R(7);

R(2) and R(3) independently of one another are —SR(4) or —COOR(5);

R(4) and R(5) independently of one another are alkyl having 1, 2, 3, 4, 5, 6, 7 or 8 carbon atoms, which is unsubstituted or is substituted by a radical from the group consisting of F, Cl, $CF_3$, methyl, $NO_2$, methoxy or NR(6)R(7); cycloalkyl having 3, 4, 5, 6 or 7 carbon atoms;

phenyl, which is unsubstituted or is substituted by a radical from the group consisting of F, Cl, $CF_3$, CN, $NO_2$, methyl, methoxy, hydroxyl or NR(6)R(7); or heteroaryl having 1, 2, 3, 4, 5, 6, 7, 8 or 9 carbon atoms, which is unsubstituted or is substituted by a radical from the group consisting of F, Cl, $CF_3$, $NO_2$, methyl, methoxy, hydroxyl or NR(6)R(7); and R(6) and R(7) are methyl.

4. The process as claimed in claim 1, wherein the compound of the formula I or salt thereof is prepared in which:

R(1) is hydrogen;

alkyl having 1, 2, 3, 4, 5 or 6 carbon atoms, which is unsubstituted or is substituted by a radical from the group consisting of F, Cl, $CF_3$, methyl or methoxy;

cycloalkyl having 1, 2, 3, 4, 5, 6 or 7 carbon atoms;

phenyl, which is unsubstituted or is substituted by a radical from the group consisting of F, Cl, $CF_3$, $NO_2$, methyl or methoxy; or heteroaryl having 1, 2, 3, 4, 5, 6, 7, 8 or 9 carbon atoms, which is unsubstituted or is substituted by a radical from the group consisting of F, Cl, $CF_3$, methyl or methoxy;

R(2) and R(3) independently of one another are —SR(4) or —COOR(5); and

R(4) and R(5) independently of one another are alkyl having 1, 2, 3, 4, 5 or 6 carbon atoms, which is unsubstituted or is substituted by a radical from the group consisting of F, Cl, $CF_3$, methyl or methoxy;

cycloalkyl having 3, 4, 5, 6 or 7 carbon atoms;

phenyl, which is unsubstituted or is substituted by a radical from the group consisting of F, Cl, $CF_3$, CN, methyl or methoxy; or heteroaryl having 1, 2, 3, 4, 5, 6, 7, 8 or 9 carbon atoms, which is unsubstituted or is substituted by a radical from the group consisting of F, Cl, $CF_3$, methyl or methoxy.

5. The process as claimed in claim 1, wherein the compound of the formula I or salt thereof is prepared in which R(1) is alkyl having 1, 2, 3, 4, 5 or 6 carbon atoms.

6. The process as claimed in claim 1, wherein the compound of the formula I or salt thereof is prepared in which R(1) is alkyl having 1, 2, 3, 4, 5 or 6 carbon atoms;

R(2) and R(3) independently of one another are —SR(4) or —COOR(5);

R(4) is alkyl having 1, 2, 3, 4, 5 or 6 carbon atoms or —$C_nH_{2n}$-phenyl where n is equal to 0, 1 or 2 and R(5) is alkyl having 1, 2, 3, 4, 5 or 6 carbon atoms.

7. The process as claimed in claim 1, wherein the compound of the formula I or salt thereof is prepared in which R(2) is —SR(4) and R(3) is —COOR(5).

8. The process as claimed in claim 1, wherein the amount of alkylphosphonic anhydride used is 0.1–5.0 mol of alkylphosphonic anhydride per mole of compound of the formula (II).

9. The process as claimed in claim 8, wherein the amount of alkylphosphonic anhydride used is 0.2–1.0 mol of alkylphosphonic anhydride per mole of compound of the formula (II).

10. The process as claimed in claim 1, wherein the alkylphosphonic anhydride used is n-propylphosphonic anhydride.

11. The process as claimed in claim, wherein the cyclization is carried out at a temperature of 10–130° C.

12. The process as claimed in claim 11, wherein the cyclization is carried out at a temperature of 20–80° C.

13. The process as claimed in claim 1, wherein the reaction time is 0.25 h to 3 days.

14. The process as claimed in claim 13, wherein the reactime is 1 to 48 h.

15. A process for synthesizing a pharmacologically active compound, which comprises reacting a compound made by the process of claim 1 under conditions sufficient to obtain the pharmacologically active compound.

16. The process as claimed in claim 1, which comprises treating the compound of formula (I) with an acid to obtain a salt of the compound of formula (I), and precipitating and filtering the resulting salt of the compound of formula (I).

17. The process as claimed in claim 16, which further comprises washing the precipitated salt of the compound of formula (I) with a solvent.

18. The process as claimed in claim 16, which further comprises recrystallizing the precipitated salt of the compound of formula (I) in a solvent.

19. The process as claimed in claim 16, which further comprises treating the precipitated salt of the compound of formula (I) with a base to obtain a compound of formula (I).

20. The process as claimed in claim 1, which comprises introducing protective groups to the compound of formula (II) before the cyclization reaction, and removing the protective groups after the cyclization reaction.

* * * * *

UNITED STATES PATENT AND TRADEMARK OFFICE

CERTIFICATE OF CORRECTION

PATENT NO. : 6,407,258 B1
DATED : June 18, 2002
INVENTOR(S) : Napierski et al.

It is certified that error appears in the above-identified patent and that said Letters Patent is hereby corrected as shown below:

Column 8,
Line 40, after “of the”, insert -- formula 1 --.

Column 12,
Line 1, “claim,” should read -- claim 1, --.
Line 8, “reactime” should read -- reaction time --.

Signed and Sealed this

Tenth Day of December, 2002

JAMES E. ROGAN
*Director of the United States Patent and Trademark Office*